US006113949A

United States Patent [19]
Brink

[11] Patent Number: 6,113,949
[45] Date of Patent: Sep. 5, 2000

[54] WEIGHT CONTROL PRODUCT AND METHOD OF TREATING HYPERLIPIDEMIA AND INCREASING VIGOR WITH SAID PRODUCT

[75] Inventor: William DesIsles Brink, Newton, Mass.

[73] Assignee: Prolab Nutrition, Inc., Bloomfield, Conn.

[21] Appl. No.: 09/179,328

[22] Filed: Oct. 27, 1998

[51] Int. Cl.[7] .......................... A61K 35/78; A61K 31/56; A61K 33/42; A61K 31/685

[52] U.S. Cl. ................... 424/602; 424/195.1; 424/196.1; 424/601; 424/603; 424/604; 424/605; 424/606; 514/78; 514/169; 514/170; 514/171; 514/177; 514/556; 514/561; 514/567; 514/574; 514/909

[58] Field of Search ............................. 424/195.1, 196.1, 424/601–606; 514/78, 169–171, 177, 556, 561, 567, 574, 909

[56] References Cited

U.S. PATENT DOCUMENTS

| | | | |
|---|---|---|---|
| 4,117,120 | 9/1978 | Elderbaum | 424/195 |
| 4,364,922 | 12/1982 | Berne et al. | 424/9 |
| 4,592,912 | 6/1986 | Nickolauss | 424/195.1 |
| 4,713,242 | 12/1987 | Trenzeluk | 12/87 |
| 4,719,111 | 1/1988 | Wilson | 424/195.1 |
| 4,847,069 | 7/1989 | Bissett et al. | 424/47 |
| 4,847,071 | 7/1989 | Bissett et al. | 424/59 |
| 5,011,843 | 4/1991 | Shell | 514/259 |
| 5,104,676 | 4/1992 | Mahmoud et al. | 426/590 |
| 5,273,747 | 12/1993 | Bombardelli et al. | 424/195.1 |
| 5,422,352 | 6/1995 | Astrup | 514/264 |
| 5,494,668 | 2/1996 | Patwardhan | 424/195.1 |
| 5,521,223 | 5/1996 | Piazza et al. | 514/785 |
| 5,587,176 | 12/1996 | Warren et al. | 424/443 |
| 5,620,965 | 4/1997 | Blank | 514/159 |
| 5,690,948 | 11/1997 | McCook et al. | 424/401 |

FOREIGN PATENT DOCUMENTS

| | | |
|---|---|---|
| 0 447 706 A1 | 3/1990 | European Pat. Off. . |
| 166998 | 4/1988 | India . |

OTHER PUBLICATIONS

Agarwal, R.C. et al., "Clinical trial of gugulipid a—new hypolipidemic agent of plant origin in primary hyperlipidemia," Indian J. Med. Res., vol. 84, pp. 626–634, Dec. 1986.

Tripathi, Y.B. et al., "Thyroid stimulating action of Z–gugulsterone obtained from Commiphora mukul," Planta Medica, 78–80, 1984.

Chemical Abstracts 125:317895, 1996.

Chemical Abstracts 127:117538, 1997.

Article by G. V. Satyavati in the Economic and Medicinal Plant Research, vol. 5, entitled "Guggulipid: a Promising Hypolipidaemic Agent from Gum Guggul (Commophora wightii)," dated 1991, pp. 49–82.

Article (Chapter 69) by Charles M. Alexander and George A. Bray in the book entitled Werner's The Thyroid, A Fundamental Clinical Text, 5th Edition, entitled "The Thyroid and Obesity," dated 1986, pp. 1458–1471.

Article by Gerald N. Burrow in The Thyroid, a Fundamental and Clinical Text, 4th Edition, entitled "Thyroid Hormone Therapy in Nonthyroid Disorders," dated 1978, pp. 974–975.

Article by Robert Cade, Michael Conte, Christian Zauner, Donald Mars, John Peterson, Denis Lunne, Norman Hommen, and David Packer in Medicine and Science in Sports and Exercise, vol. 16, No. 3, entitled "Effects of Phosphate Loading on 2,3–Diphosphoglycerate and Maximal Oxygen Uptake," dated 1984, pp. 263–268.

Article by Marcia A. Johnson, Kim Tekkanat, Stephen P. Schmultz, and Irving H. Fox in The American Society for Clinical Investigations, Inc., vol. 84, entitled "Adenosine Triphosphate Turnover in Humans," dated 1989, pp. 990–995.

Article by Mark Farber, M.D., Stefano Carlone, M.D., Paolo Palange, M.D., Piero Serra, M.D., Vincenzo Paoletti, M.D.; and Naomi Fineberg, Ph.D., entitled "Effect of Inorganic Phosphate in Hypoxemic Chronic Obstructive Lung Disease Patients During Exercise," Aug. 1987, pp. 310–312.

Article by Janis S. Fisler, Ph.D. and Ernest J. Drenick, M.D. in The American Journal of Clinical Nutrition, Jul. 1884, entitled "Calcium, Magnesium, and Phosphate Balances During Very Low Calorie Diets of Soy or Collagen Protein in Obese Men: Comparison to Total Fasting," pp. 14–25.

Article by Irwin A. Rose, Jessie V. B. Warms, and Edward L. O'Connell in Biochemical and Biophysical Research Communications, vol. 15, No. 1, 1964, entitled "Role of Inorganic Phosphate in Stimulating the Glucose Utilization of Human Red Blood Cells," pp. 33–37.

Article by Mark O. Farber, Thomas Y. Sullivan, Naomi Fineberg, Stefano Carlone, and Felice Manfredi in J. Lab. Clin. Med., vol. 104, No. 2, entitled "Effect of Decreased $O_2$ Affinity of Hemoglobin on Work Performance During Exercise in Health Humans," dated 1983, pp. 166–175.

Article by James L. Fry, Jr., BA and Herbert J. Proctor, MD., FACS, entitled "Rapid Increase in Red Cell 2,3–DPG in Hypoxic Rabbits Following Infusion of Inosine, Pyruvate, and Inorganic Phosphate," date unknown, pp. 220–221.

(List continued on next page.)

Primary Examiner—John Pak
Attorney, Agent, or Firm—Donald O. Nickey; Standley & Gilcrest L.L.P.

[57] ABSTRACT

This invention relates to a weight control composition, preferably in the form of a capsule or tablet, comprising a mixture of guggul extract and at least one phosphate salt selected from calcium phosphate, potassium phosphate and sodium phosphate. The composition evidences synergistic activity in reducing body weight and percent body fat in mammals. The guggul extract/phosphate salt product also reduces plasma lipid levels and cholesterol in overweight hyperlipidaemic humans. The inventive composition may also contain at least one additional component selected from phosphatidylcholine, hydroxycitric acid and L-tyrosine.

8 Claims, No Drawings

OTHER PUBLICATIONS

Article by Kenneth D. Fine, M.D., Frederick Ogunji, Ph.D., Robin Florio, BS, Jack Porter, MS, and Carol Santa Ana, BS, in Digestive Diseases and Sciences, vol. 3, No. 12, Dec. 1998, entitled "Investigation and Diagnosis of Diarrhea Caused by Sodium Phosphate," pp. 2708–2714.

Internet Article by Kaciuba–Uscilko H; Nazar K; Chwalbinksa–Moneta J; Ziemba A; Kruk B; Szczepanik J; Titow-–Stupnicka E; Bicz B, entitled "Effect of Phosphate Supplementation on Metabolic and Neuroendorine Responses to Exercise and Oral Glucose Load in Obese Women During Weight Reduction," National Library of Medicine: IGM Full Record Screen, Dec. 1993, 2 pages.

Internet Article by Nazar K; Kaciuba–Uscilko H; Szezepanik J; Zemba AW; Kruk B; Chwalbinska–Moneta J; Titow–Stupnicka E; Bicz B; Krotkiewski M entitled "Phosphate Supplementation Prevents a Decrease of Triiodothyronine and Increases Resting Metabolic Rate During Low Energy Diet," National Library of Medicine; IGM Full Record Screen, Jun. 1996, 2 pages.

Comments to the Editor by Thomas Yannios, M.D., "Effects of Phosphates", date unknown, p. 446.

Nazar et al., Phosphate Supplementation Prevents A Decrease of Triiodothyronine and Increases Resting Metbolic Rate During Low Enery Diet, J. Physiology and Pharmacology 1996, 47(2), 373–383.

Kaciuba–Uscilko et al., Effect of Phosphate Supplementation on Metabolic and Neuroendocrine Responses to Exercise and Oral Glucose Load in Obese Women During Weight Reduction Physiology and Pharmacology 1993, 44(4), 425–440.

Tripathi et al., Thyroid Stimulatory Action of (Z)–Guggulstrone: Mechanism of Action, Plant medica 1988, 271–277.

Colker et al., Effects of a Standardized Guggalsterone Extract and Phosphate Salts Based Products on Body Weight and Body Fat of Healthy Overweight Adults, Medicine and Sports in Sports and Exercise, vol. 31(5), pages: first four pages, 1999.

IntelliHEALTH, Phosphates, <Ipn.intellhealth.com>, No Date Available.

WEIGHT CONTROL PRODUCT AND METHOD OF TREATING HYPERLIPIDEMIA AND INCREASING VIGOR WITH SAID PRODUCT

FIELD OF THE INVENTION

This invention relates generally to a weight control product that is administered enterally to mammals in need of losing weight and/or reducing the blood plasma lipid levels. The weight control product comprises a mixture of guggul extract and phosphate salts. The inventive product is also useful in enhancing mood states, increasing vigor and reducing blood serum lipid levels.

BACKGROUND OF THE INVENTION

The weight control product of the present invention is designed to promote weight loss as a component of a weight control program for individuals who are overweight and desire to lose body fat and/or reduce their plasma lipid levels. The product according to the invention is consumed as a nutritional supplement and is preferably incorporated into a multi-disciplinary nutritional program such as the American Heart Association Step One Diet.

Numerous weight control products are known in the literature. One example of a weight control product is taught in U.S. Pat. No. 4,959,227 to Amer wherein the product has a reduced lactose content and contains dietary fiber. In similar fashion, U.S. Pat. No. 5,104,676 to Mahmoud et al. discloses a weight loss product that utilizes a particular blend of soluble, insoluble, fermentable and non-fermentable fibers. Commercially available weight control products include Ultra-Slim Fast® which is distributed by Slim Fast Foods, a division of Thompson Medical Company, Inc. New York, N.Y. and OpitiTrim® which is available from the Clinical Products Division of Sandoz Nutrition Corp., Minneapolis, Minn. In addition, literally hundreds of chemical entities have been suggested as weight loss products, however, none of the prior art has suggested or disclosed the combined use of a guggul extract with a blend of phosphate salts to result in a composition that is highly effective in reducing the weight of a mammal through primarily a loss of body fat while at the same time dramatically decreasing the blood plasma lipid levels of the individual, enhancing the mood states and increasing vigor.

A compound known as Z-guggulsterone has been identified as having the following structural formula:

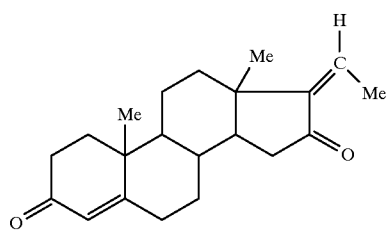

The E-stereoisomer has also been identified and these ketones are known hypolipemic and antiplatelet aggregation agents. A process for the preparation of pharmacologically active synthetic Z and E stereoisomeric mixture of guggulsterones is disclosed in EP0447,706 to Hamied. These compounds have also been isolated from the exudate of a plant known as *Commiphora mukul* (Hook, ex stocks) Engl. (syn. *Balsamodendron mukul* Hook) which is a small tree of the Burseraceae family, endemic in the Indian peninsula. If the trunk is etched, the plant emits a yellowish gummy exudate, which coagulates rapidly in the form of stalactites having a balsamic smell. In the ancient Sanskrit, this gum resin is called guggulu and is a product which is still used in Indian popular medicine for the treatment of obesity and some arthritic diseases. Recently, a lipophilic extract has been prepared from this resin, this extract contains many classes of compounds, among which lignans, terpenes and some keto-steroids, named Guggulsterones. Hypolipidemic and platelet aggregation inhibiting activities are described for this lipophilic extract, which is normally obtained by simple resin extraction with ethyl acetate, or for Guggulsterone-Z and Guggulsterone-E, whose components in the extract are normally titrated.

By studying this resin, it has unexpectedly been found that the lipophilic extract with ethyl acetate or some fractions obtained from it when combined with a mixture of phosphate salts demonstrates outstanding weight loss, fat loss, mood elevating and hyperlipidemic properties. Further, the synergistic action of the extract and mixture of phosphate salts has demonstrated efficacy in elevating the vigor of individuals consuming it.

The extract is prepared by etching *Commiphora mukul* bark and obtaining the resin from it. The resin is then dried, ground and subjected to extensive extraction with ethyl acetate. The collected extracts may then be treated with charcoal. After charcoal separation, the colorless solution is concentrated to obtain a thick paste, which is recovered with ethanol, and, after filtrating the insoluble matter, concentrated with complete solvent removal.

Indian Complete Specification No. 166998 discloses a method for the manufacture of a pharmaceutical composition of guggulipid in solid dosage form. The guggulipid is disclosed as being mixed with excipients and granulating agents and thereafter pressed into the solid dosage form. This reference also states that in biological tests in rats and mice with the dosage form, pharmacological activities such as hypolipedemic, antiobesity and hypocholesterolemic were observed.

U.S. Pat. No. 5,273,747 to Bombardellie et al. discloses that the *Commiphora mukul* lipophilic extracts have therapeutic applications in the treatment of inflammations of the skin and external mucosa and in the symptomatic treatment of benign prosthetic hypertrophy and in the treatment of acne.

A study of the effects of guggulsterone on hypolipidemia is reported in an article by Beg, et al. Indian-J-Physiol-Pharmacol. 1996 July; 40 (3): 237–40. This article reports that the administration of guggulsterone in daily divided doses of 75 mg for a period of eight (8) weeks together with supportive measures like a high protein diet, diuretics and hematinics resulted in a significant reduction of total serum lipid and total serum cholesterol. No mention is made of weight loss in this publication, nor is it suggested to combine the guggulsterone with a mixture of phosphate salts to produce synergistic effects.

In an article published by Tripathia, et al. entitled Thyroid Stimulatory Action of Z-Guggulsterone: Mechanism of Action. Planta-Med., 1988 August; 54(4): 271–7 the authors disclose that guggulsterone is effective in stimulating the activity of the thyroid gland in rats. The guggulsterone used in this study is disclosed as being a ketosteroid isolated from the oleoresin of the dry exudate of *Commiphora mukul*. The compound was shown to counteract the thyroid suppressant activity of a known thyroid inhibitor (carbimazole).

Agarwal, et al. investigated the use of gugulipid as a hyperlipidemic agent. Indian-J-Med-res. 1986 December;

84:626–34. In similar fashion, guggulsterones have also been found to be very effective in reducing total cholesterol levels and LDL levels. Nityanand et al. report in "Clinical Trials With Gugulipid, A New Hyperlipidaemic Agent" J-Assoc-Physicians-India, 1989 May; 37(5): 323–8, a multi-center clinical trial with 205 patients over a twelve (12) week period. A gugulipid dose of 500 mg twice daily after eight (8) weeks showed a significant lowering in the serum cholesterol (average 23.6%) and serum triglycerides (average 22.6%). The study also used colfibrate as a comparative. The gugulipid average fall in serum cholesterol and triglycerides was 11 and 16.8% respectively and with colfibrate 10 and 21.6% respectively. The lipid lowering effect of both drugs became evident three (3) to four (4) weeks after starting the drugs. Nityanand et al. also reported that hypocholesterolemic patients responded better to gugulipid therapy than hypertriglyceridemic patients who responded better to colfibrate therapy. HDL-cholesterol was increased in sixty percent (60%) of the cases who responded to the gugulipid therapy, in contrast colfibrate had no effect on HDL-cholesterol.

U.S. Pat. No. 5,690,948 to McCook et al. discloses gugulipid (a lipophilic ethyl acetate extract from C. Mukul or C. Wightii) and an alcoholic fraction of gugulipid as an antisebum and/or antioxidant for skin care compositions. This patent does not suggest or disclose the combination of gugulipid with a mixture of phosphate salts to create a weight control product. One important aspect of the inventive weight control product is the synergistic effect that is obtained by combining the guggul extract with a sufficient amount of phosphate salts.

A number of studies have recently investigated the effect of calcium phosphate, potassium phosphate and sodium phosphate to increase the basal metabolic rate (BMR) and increase thyroid activity. For example, see Nazar et al. "Phosphate Supplementation Prevents A Decrease In Triiodothyronine And Increases Resting Metabolic Rate During Low Energy Diet" J-Physiol-Pharmacol. 1996 June; 47(2): 373–83. In the Nazer et al. study thirty (30) over-weight women participated in an eight (8) week slimming program consisting of a self controlled, low energy diet (4.2 MJ per day) supplemented with highly viscous fibers and mineral tablets containing calcium, potassium and sodium phosphates. This was a double blind, cross-over study. During periods of phosphate supplementation, the resting metabolic rate (RMR) increased by approximately twelve percent (12%) (p<0.05) in group one and nineteen percent (19%) (p<0.05) in group two. The study reported that there were no differences between groups in the plasma insulins catecholamine, growth hormone, cortisol and testosterone levels. It was also reported that phosphate supplementation did not effect plasma lipids or blood glucose concentration.

Kaciuba et al. reported in "Effective Phosphate Supplementation On Metabolic and Neuroendocrine Responses To Exercise And Oral Glucose Load In Obese Women During Weight Reduction" J-Physiol-Pharmacol 1993 December; 44(4): 425–40; a study wherein 36 obese women participated in a four (4) week weight reducing program. All of them complied with a low fat diet of approximately one thousand (1000) calories per day with high viscous fiber capsules as a basic supplement. Group One (n=18) received mineral tablets containing mainly calcium and potassium phosphates while the remaining subjects (Group Two) were given a placebo tablet. This study reports that weight loss during energy restriction was not affected by phosphate supplementation, however, the phosphates caused a significant increase (p<0.05) in the resting metabolic rate.

For every form of life, phosphates play an essential role in all energy transfer processes such as metabolism, photosynthesis, nerve function, and muscle action. The nucleic acids, which among other things make up the hereditary material (the chromosomes) are phosphates, as are a number of coenzymes. The phosphates are based on phosphorus atoms tetrahedrally surrounded by oxygen atoms, with the lowest member of the series being the simple $PO_4^{-3}$ anion (the orthophosphate ion). The phosphorus compound of major biological importance is adenosinetriphosphate (ATP), which is an ester of the salt, sodium tripolyphosphate, widely employed in detergents and water softening compounds. Practically every reaction in metabolism and photosynthesis involves hydrolysis of this tripolyphosphate to its pyrophosphate derivative, called adenosinediphosphate (ADP).

Phosphates are used as dietary supplements for patients who are unable to get enough phosphorus in their regular diet, usually because of certain illnesses or diseases. Injectable phosphates are administered only by or under the supervision of a health care professional. Various forms of phosphates are available without a prescription. Often tablets and powders are dissolved in a liquid prior to consumption. This is done to avoid or lessen possible side effects which include diarrhea, nausea, vomiting and stomach pain.

While the prior art discloses the use of guggulsterones to reduce blood plasma lipid content and the use of phosphates to decrease triiodothyronine and increase resting metabolic rate, there is no suggestion or disclosure of combining these materials to achieve a synergistic effect in weight control and the surprising benefits of enhanced mood states and increased vigor.

SUMMARY OF THE INVENTION

There is disclosed a weight control product comprising guggul extract and at least one phosphate salt. There is also disclosed a method for reducing the plasma lipid levels and/or cholesterol levels in a mammal, said method comprising the step of administering to said mammal a therapeutically effective amount of a composition comprising guggul extract and at least one phosphate salt. There is also disclosed methods for enhancing the mood states and vigor of a mammal, the methods comprising the enteral administration of a guggul extract/phosphate salt composition.

There is further disclosed a guggul extract/phosphate salt weight control product comprising at least one additional component selected from the group consisting of phosphatidylcholine, hydroxycitric acid (HCA) and L-tyrosine. In yet another embodiment of the invention, the weight control product comprises a mixture of phosphate salts selected from the group consisting of calcium phosphate, potassium phosphate and sodium phosphate. More specifically, the calcium phosphate and potassium phosphates are dibasic, while the sodium phosphate may be a mixture of monobasic and dibasic. There is further disclosed a method for enhancing the fat loss in a mammal, said method comprising the administration of a composition comprising guggul extract and at least one phosphate salt.

In a preferred embodiment, the weight control product according to the invention, comprises phosphatidylcholine, calcium phosphate (dibasic), potassium phosphate (dibasic), sodium phosphate (monobasic), sodium phosphate (dibasic), guggul extract, HCA, and L-tyrosine. In the weight control product according to the invention the guggul extract and the phosphate salts are in weight ratios of from 1 to 5 to 5 to 1.

DETAILED DESCRIPTION OF THE INVENTION

As used herein "enteral administration" means consumption orally or application to the stomach or intestines.

As used herein "pharmaceutically acceptable" means that salts, drugs, medicaments, or other ingredients which the term describes are suitable for use in mammals without undue toxicity, incompatibility, instability, irritation, allergic response, and the like commensurate with a reasonable benefit/risk ratio.

As used herein and in the claims the term "therapeutically effective amount" means an amount of compound or composition sufficient to significantly induce a positive modification in the condition to be treated, but low enough to avoid serious side effects (at a reasonable benefit/risk ratio) within the scope of sound medical judgment. The therapeutically effectively amount of the compound or composition will vary with the particular condition being treated, the age and physical condition of the patient being treated, the severity of the condition, the duration of the treatment, the nature of concurrent therapy, the specific compound or composition employed, the particular pharmaceutically acceptable compound utilized, and like factors within the knowledge and expertise of the medical community.

As used herein and in the claims the term "guggul extracts" means that composition extracted from the plants of the genis commiphora, particularly *Commiphora mukul* or *Commiphora wightii* or the chemically synthesized active components thereof. The guggul extract is obtained from the gum/resin of these plants, shrubs, or trees and is a complex mixture of terpenes, sterols, esters, and higher alcohols. The ethylacetate extract of the resin is an oily material also known as "gugulipid" or "guggal lipid". The pharmacological activity of gugulipid is attributed to two known ketonic steroids (the E- and Z- guggulsterones). The guggul extract contains from 5–50% by weight of the guggulsterones, more preferably at least 10% by weight. In an embodiment of the invention the "guggul extract" can be prepared in accordance with techniques known in the art, see for example EP0447,706.

As used herein and in the claims the term "vigor" means active bodily or mental strength or force. Vigor is also intensity of action or effect and is evidenced by active, healthy, well balanced mental and physical states. Feelings of vigor or fatigue can be assessed through a Profile of Mood States questionnaire (POMS) (Educational and Industrial Testing Service, San Diego. Calif.). The POMS questionnaire has been validated as a method to determine significant differences in subjective feelings subject while undergoing a clinical trial.

The weight control product according to the invention is enterally/orally administered to a mammal in need of weight control. The product according to the invention may also be consumed by individuals not in need of weight loss, but in need of reducing blood serum lipid and cholesterol levels. Further, individuals that would simply like to increase their energy levels or vigor, can benefit from the composition of this invention. The weight control product may be administered in the form a capsule, tablet, powder, liquid, food bar, soft gel capsule and the like. The form of administration is not important, however, dosages of at least 5 mg of guggul extract per kilogram of body weight and at least 15 mg of phosphate salt per kilogram of body weight should be administered daily. More preferably, the mammal is enterally administered at least 10 mg of guggul extract per kilogram of body weight and at least 20 mg of phosphate salts per kilogram of body weight per day. Thus, for a typical human of 70 kilograms the dose should be at least 350 mgs of guggul extract (assume 10% by weight guggulsterones) and at least 1050 mgs of phosphate salts per day. A typical dose can range as high as 2 gms per day of the guggul extract and 3 gms per day for the phosphate salts. In an embodiment of the invention the daily dose of guggulsterones for an adult is about 75 mg and about 1,650 mg for the phosphate salts.

The phosphate salt component is preferably a mixture of sodium, potassium and calcium phosphates. The weight ratio of calcium phosphate to potassium phosphate to sodium phosphate can range from 5:1:5 to 1:5:1. A preferred weight ratio is about 2:1:1. The blend of the phosphate salts is designed to keep the mineral load from any one source, such as sodium, to a minimum and thus reduce the possibility of an electrolyte imbalance.

The L-tyrosine, useful in the weight control product of the present invention, is the naturally occurring laveorotatory amino acid. Tyrosine is also known as p-hydroxyphenylalanine of the molecular formula $C_9H_{11}NO_3$ and is a readily available amino acid that is typically obtained from protein hydrolysis. The amount of tyrosine consumed per day can range from 5 to 100 mg per kilogram of body weight.

The phosphatidylcholine useful in the product according to the invention is also known as lecithin. Phosphatidylcholine is a polar lipid that occurs in crude fats and oils and is also associated with egg yolk. The phosphatidylcholine useful in the product of this invention can be derived from soybean oil and is readily available from commercial sources such as Lucas Meyer, Inc. of Dekator, Ill. The phosphatidylcholine may be combined with other phospholipids such as phosphatidylserine, phosphatidylethanolamine and phosphatidylinositol can also be included in the inventive product. The dose of phosphatidylcholine per day is at least 0.1 mg, preferably at 1.0 mg per kg of body weight.

*Garcinia cambosia* is the preferred source of hydroxycitric acid. Hydroxycitric Acid (HCA) is a compound extracted from the rind of the fruit *Garcinia cambogia* or synthetically produced. Other sources of HCA include beet sugar, *Hibiscus sabdariffa*, *Garcinia indica* and *Garcinia atroviridus*. HCA is available commercially and can be prepared from the garcinia fruit peel in accordance with U.S. Pat. No. 5,536,516. The ester and amide derivatives of HCA are also useful in the product according to the present invention. These derivatives are described in U.S. Pat. No. 4,028,397 and 4,007,208.

The phosphates useful in the product, according to the invention, include the calcium, potassium and sodium phosphates. The monobasic and dibasic varieties are useful and the polyphosphates commonly have two or three phosphorus atoms per molecule but polymeric forms with more than twenty phosphorus atoms have application. As mentioned previously, the phosphate salts are preferably a mixture of calcium, potassium and sodium salt.

The present invention will be further illustrated by the following examples.

EXAMPLE 1

Preparation of Guggulsterone-phosphate Salt Product

The ingredients for making a 5.5 kg batch of the weight control product according to an embodiment of the invention is listed in Table 1. The extract of *commiphora mukul* was obtained from Ayurveda of Bellevue, Wash. The extract was a cream colored powder. It contained about 10.7% by weight guggulipids.

TABLE 1

Batch Preparation of Product

| Ingredient | gms |
| --- | --- |
| Lecithin (20% phosphatidylcholine) | 437 |
| Calcium Phosphate (dibasic 23%) | 875 |
| Potassium Phosphate (dibasic $K^+$ 44.8%, P 17.8%) | 525 |
| Sodium Phosphate (monobasic $Na^{++}$ 9.16%) | 262 |
| Sodium Phosphate (dibasic $Na^{++}$ 32%) | 262 |
| Guggul Extract (10% guggulsterones by wt.) | 875 |
| Garcinia Cambogia (50% hydroxycitric acid by wt.) | 875 |
| L-Tyrosine | 875 |
| Silicon Dioxide | 35 |
| Magnesium Stearate | 70 |
| Rice (powder) | 367 |

The first step in manufacturing a weight control product, according to the invention, was to mix all ingredients except for the silicon dioxide and magnesium stearate in a blender for 15 minutes. The silicon dioxide and the magnesium stearate were screened through a #40 mesh screen and then added to the blender. Blending continued for an additional 10 minutes and then the weight loss product was placed into #00 hard gelatin capsules to a gross weight of 860 mg per capsule. The dose per capsule of the various active components is found in Table 2.

TABLE 2

Gelatin Capsules

| Ingredient | Dose per capsule |
| --- | --- |
| Phosphatidylcholine | 12.5 mg |
| Calcium Phosphate dibasic 23% | 125.0 mg |
| Potassium Phosphate (dibasic $K^+$ 44.8%, P 17.8%) | 75.0 mg |
| Sodium Phosphate (monobasic $Na^{++}$ 9.16%) | 37.5 mg |
| Sodium Phosphate (dibasic $Na^{++}$ 32%) | 37.5 mg |
| Guggul Extract (10% guggulsterones by wt.) | 125.0 mg |
| Garcinia Cambogia (50% hydroxycitric acid by wt.) | 125.0 mg |
| L-Tyrosine | 125.0 mg |
| Total | 712.5 mg |

EXAMPLE 2

Clinical Study

This experiment was conducted to determine the effects of the guggul extract/phosphate salt weight loss product of the present invention on body composition, plasma lipid levels and mood states in overweight hyperlipidemic adults. A double blind, placebo controlled protocol was developed wherein twenty (20) subjects with a mass index (BMI) of greater than twenty five (>25) were divided into three groups. Group A received 750 mgs of guggul extract and 1,650 mgs phosphate daily (6 capsules from Table 2). Group B received a maltodextrine placebo while Group C received nothing (control) for six weeks. The subjects were instructed by a registered dietitian to follow an American Heart Association Step One Diet and a three day per week circuit exercise program which was supervised by an exercise physiologist.

Subjects were excluded from the study if they were currently following a reduced calorie diet, were taking anorectic medications (i.e. phentermine, silbutramine, etc.), had a history of thyroid disease, HIV/AIDS, cancer or any wasting syndrome. Subjects were also excluded if they had never exercised before. Capsules for Group A and Group B were the same in terms of size, shape, color and weight. Each group was instructed to take six capsules per day, two with each main meal.

Each subject was evaluated at baseline, week three, week six, and conclusion. Total body weight was measured using a Detecto™ balanced medical scale at each laboratory visit. Subjects were weighed after a four hour fast and voiding of the bladder. After four hours of fasting, body composition was measured via bioelectric impedance analysis (Biodynamics 3.10, Seattle. Wash.). All participants refrained from caffeine the day prior to body composition analysis and subjects were prohibited from drinking alcohol throughout the study.

All subjects engaged in a three day a week circuit training exercise program under the guidance of an exercise physiologist. The exercise sessions lasted for about forty-five (45) minutes. The exercise program consisted of a combination of step aerobics and weight training. The subjects were requested to stay on the 1800 calorie American Heart Association Step One Diet and were given meal plans, daily menus and restaurant guidelines. Each subject also was followed up by telephone from a registered dietitian and multiple twenty-four (24) hour dietary recalls were also taken at baseline, week three and week six.

Perceived Energy

The subjects of the study were also evaluated to determine if the inventive weight control product had any impact on the subjects feelings of vigor or fatigue. A Profile of Mood States questionnaire (POMS) was employed to determine if the supplementation had any impact on these feelings. The questionnaire was from the Educational and Industrial Testing Service of San Diego, Calif. The POMS questionnaire has previously been validated as a method to determine significant differences in subjective feelings while participating in a study. Each subject took the POMS at each laboratory visit.

Biochemical Parameters

Serum chemistries, complete blood count, total cholesterol and triglycerides were assessed at baseline, week 3, and week 6 during scheduled laboratory visits. The blood was drawn via the antecubital vein and processed by Quest Diagnostics, Wallingford, Conn. Urinalysis was also conducted at each laboratory visit (Chemstrip Analyzer, Indianapolis, Ind.) and tested for any effect on urinary glucose or protein. Specific gravities were also measured as an indication of concentrated urine and dehydration.

Statistical analysis was conducted for each group and was tested for intergroup and intragroup variance. Fisher's exact test was utilized for baseline characteristics of the three groups while a Kruskal-Wallis Test was employed to test the continuous variables. Significance was set at a p value of <0.05. A total of twenty (20) patients enrolled however, two subjects dropped out therefore, a total of eighteen (18) patients completed the study.

Results

The treatment group (Group A) lost a significant amount of body weight as compared to the placebo and controls groups. Group A lost 3.14% body weight (p<0.05). Group A lost a total of 2.54 kg (5.59 pounds) or 0.4 kg (0.9 pounds) per week. Group A also had a significant reduction in their fatigue as compared to other groups, that is, they felt less tired over time with the supplement according to the present invention. Group A also experienced a significant increase in vigor as they felt more energetic (24%) over time with the supplement. A significant decrease in body fat was also seen in Group A. All three groups lost a percentage of body fat however, Group A lost twice as much body fat than the placebo or control groups—A=3.8%; B=1.78%; C=1.75%; (p<0.01). In terms of actual fat weight loss, Group A lost 4.3 kg (9.48 pounds) of actual fat whereas the placebo group lost 1.36 kg (3 pounds) and the control group lost 1.22 kg (2.9 pounds) (p<0.01). The magnitude of lost fat for Group A was therefore three times that of all other groups. From another prospective, Group A lost 63% more fat than the placebo and control groups. An analysis of the blood chemistries also demonstrated that Group A experienced a trend towards better blood sugar values and that thyroid efficiency improved somewhat.

EXAMPLE 3

Comparative Analysis

This experiment is conducted to determine the active components of the composition disclosed in Table 2. In a manner similar to that described in Example 1, four formulas are prepared wherein Formula A is according to Table 1 in Example 1, Formula B omitted the calcium salts and the guggul extract, Formula C omitted the guggul extract and Formula D omitted the phosphate salts. The omitted substance is replaced with maltodextrin to keep the per capsule dosages for the remaining components identical. The clinical study is similar to that disclosed in Example 2 however, the study group is divided into 4 groups. Group A received six capsules daily of the formula disclosed in Table 1, while Groups B, C and D received six capsules of Formula B, C and D respectively. Table 3 sets forth the compositions of Formulae B, C and D.

TABLE 3

| Ingredient | Dose per capsule Formula B | Dose per capsule Formula C | Dose per capsule Formula D |
|---|---|---|---|
| Phosphatidylcholine | 12.5 mg | 12.5 mg | 12.5 mg |
| Calcium Phosphate (dibasic 23%) | 0 | 125.0 mg | 0 |
| Potassium Phosphate dibasic K⁺ 44.8%, P 17.8% | 0 | 75.0 mg | 0 |
| Sodium Phosphate (monobasic Na⁺⁺ 9.16%) | 0 | 37.5 mg | 0 |
| Sodium Phosphate (dibasic Na⁺⁺ 32%) | 0 | 37.5 mg | 0 |
| Guggul Extract (10% guggulsterones by wt.) | 0 | 0 | 125.0 mg |
| Garcinia Cambogia (50% hydroxycitric acid by wt.) | 125.0 mg | 125.0 mg | 125.0 mg |
| L-Tyrosine | 125.0 mg | 125.0 mg | 125.0 mg |
| Maltodextrin | 400.0 mg | 125.0 mg | 275.0 mg |

In terms of actual fat weight loss Group A will lose about 4.3 kg, Group B about 1.3 kg, Group C about 1.4 kg and Group D about 1.6 kg of fat. This test evidences that the combination of the guggul extract and the phosphate salts is critical to the extraordinarily high loss of body fat in the subjects. The guggul extract interacts synergistically with the phosphate salts to result in enhanced weight and fat loss. Similar to the results found in Example 2, the POMS ratings of Group A are significantly better than Groups B, C and D. In conclusion, the guggul extract/phosphate salt weight loss product improved mood states with favorable body composition changes.

Industrial Applicability

The weight control product of the invention provides an unexpected benefit in weight loss, fat loss, mood elevation and the lowering of blood plasma lipid levels. The medical community and consumers at large will readily accept the inventive product as it provides outstanding results and is economically produced, with no known side effects.

While certain representative embodiments and details have been described for the purpose of illustrating the invention, it will be apparent to those skilled in the art that various changes and modifications may be made therein without departing from the spirit or scope of the invention.

What is claimed:

1. A weight control product comprising guggul extract and at least one phosphate salt selected from the group consisting of sodium phosphate, potassium phosphate and calcium phosphate, wherein the weight ratio of said guggul extract to said at least one phosphate salt is from 1:5 to 5:1.

2. The weight control product according to claim 1 additionally comprising at least one component selected from the group consisting of phosphatidylcholine, hydroxycitric acid and L-tyrosine.

3. The weight control product according to claim 1 where in the phosphate salts are a mixture of calcium phosphate dibasic, potassium phosphate dibasic, sodium phosphate monobasic and sodium phosphate dibasic.

4. The product according to claim 1 wherein said guggul extract contains from 5–50% by weight of guggulsterones.

5. The product according to claim 4 wherein said extract is an ethylacetate of resin from a plant selected from *Commiphora mukul* and *Commiphora wightii*.

6. The product according to claim 5 wherein said at least one phosphate salt is a mixture of calcium phosphate, potassium phosphate and sodium phosphate at weight ratio of from 5:1:5 to 1:5:1.

7. The product according to claim 6 additionally comprising at least one component selected from the group consisting of phosphatidylcholine, hydroxycitric acid and L-tyrosine.

8. A composition comprising guggul extract, at least two phosphate salts selected from the group consisting of sodium phosphate, potassium phosphate and calcium phosphate, wherein the weight ratio of said guggul extract to said at least one phosphate salt is from 1:5 to 5:1, and at least one component selected from the group consisting of phosphatidylcholine, hydroxycitric acid and L-tyrosine.

* * * * *